United States Patent [19]

Barwick, Jr.

[11] Patent Number: 5,766,146
[45] Date of Patent: Jun. 16, 1998

[54] METHOD OF INFUSION CONTROL DURING PHACOEMULSIFICATION SURGERY

[75] Inventor: Billie John Barwick, Jr., Beverly, Mass.

[73] Assignee: Allergan, Waco, Tex.

[21] Appl. No.: 627,489

[22] Filed: Apr. 4, 1996

[51] Int. Cl.[6] .................................................. A61M 1/00
[52] U.S. Cl. ............................ 604/28; 604/31; 604/65
[58] Field of Search .............................. 604/65, 30, 31, 604/69; 128/748

[56] References Cited

U.S. PATENT DOCUMENTS

| | | | |
|---|---|---|---|
| 3,693,613 | 9/1972 | Kelman | 128/24 A |
| 4,019,514 | 4/1977 | Banko | 604/31 |
| 4,496,342 | 1/1985 | Banko | 128/683 |
| 4,841,984 | 6/1989 | Armeniades et al. | 128/748 |
| 4,983,901 | 1/1991 | Lehmer | 318/685 |
| 5,154,696 | 10/1992 | Shearing | 604/22 |
| 5,268,624 | 12/1993 | Zanger | 318/551 |
| 5,360,398 | 11/1994 | Grieshaber et al. | 604/30 |
| 5,417,246 | 5/1995 | Perkins et al. | 137/870 |

FOREIGN PATENT DOCUMENTS

| | | |
|---|---|---|
| 7801269 | 1/1978 | France . |
| 3713420 | 11/1988 | Germany . |
| 9520374 | 8/1995 | WIPO . |

OTHER PUBLICATIONS

Blumenthal et al., "Using an Anterior Chamber Maintainer to Control Intraocular Pressure During Phacoemulsification," *J. Cataract & Refract. Surg.*, vol. 20, Jan. 1994, pp. 93–96.

*Primary Examiner*—Michael Buiz
*Assistant Examiner*—Julian W. Woo
*Attorney, Agent, or Firm*—Walter A. Hackler

[57] ABSTRACT

A method for minimizing excess intraocular pressure during a phacoemulsification procedure in which eye tissue is fragmented and aspirated from the eye through a needle with irrigation fluid includes controlling the rate of irrigation fluid flow rate upon partial or total occlusion of the needle. For example, the method may include the steps of: introducing irrigation fluid into an eye at a selected rate; thereafter aspirating said irrigation fluid while introducing the irrigation fluid at a higher rate; during phacoemulsification and aspiration of fragmented eye tissue through the needle, introducing the irrigation fluid at the higher rate; and upon partial occlusion of the needle with fragmented eye tissue, introducing the irrigation fluid at a still higher rate.

10 Claims, 3 Drawing Sheets

METHOD OF INFUSION CONTROL DURING PHACOEMULSIFICATION SURGERY

The present invention is generally directed to a method for controlling the flow of irrigation fluid from a source to a patient in connection with medical treatments. The flow of fluid to and from a patient through a fluid infusion or extraction system is many times critical to the procedure being performed, such as in ophthalmic microsurgery in which surgical instruments such as electromechanical or pneumatically driven cutters and phacoemulsification instruments are commonly employed. These instruments require a source of fluid to infuse a surgical site and a source of negative pressure to evacuate the infused liquid and debris from the site.

A number of medically recognized techniques has been utilized for lens removal and among these, a popular technique is phacoemulsification. This method includes the making of a corneal incision, which is typically cauterized to reduce bleeding, and the insertion of a handheld surgical implement which includes a needle which is ultrasonically driven in order to emulsify, or fragment, the eye lens. Simultaneously with this emulsification, a fluid is inserted for irrigation of the emulsified lens and a vacuum provided for aspiration of the emulsified lens and inserted fluids. During this procedure care must be exercised to maintain intraocular pressure (IOP) within certain limits to prevent damage to the eye chamber.

The hereinabove described phacoemulsification techniques are well-known in the field of ophthalmology going back to the late 1960s. A full discussion of phacoemulsification is found in Chapter 11, "The Mechanics of Phacoemulsification; Chapter 12, "The Phacoemulsification Procedure"; Chapter 13, "Cataract removal by Phacoemulsification"; and Chapter 14, "Small Pupil Phacoemulsification Techniques of *The Surgical Rehabilitation of Vision— An Integrated Approach to Anterior Segment Surgery*, edited by Lee T. Norman, W. Andrew Maxwell and James A. Davison, Gower Medical Publishing, New York, N.Y., 1992, ISBN 0-397-44693-4. Chapters 11–14 thereof are incorporated herein in their entirety by reference for the purpose to describing phacoemulsification procedures.

Phacoemulsification systems have control units that include a variable speed peristaltic pump a vacuum sensor, an adjustable source of ultrasonic power and a programmable microprocessor with operator-selected presets for controlling aspiration rate, vacuum and ultrasonic power levels. Operation of such systems is described in U.S. patent application Ser. No. 08/378,533 filed Jan. 24, 1995 entitled "Method and Apparatus for Controlling Irrigation and Aspiration of Fluids During Surgical Procedures on the Eye" and is incorporated herein in its entirety for the purpose of describing a phacoemulsification system useful in the method of the present invention.

It should be apparent that the control of hand-held surgical instruments for use in phaco surgery is complex. Phacoemulsifier apparatus typically comprises a cabinet, including a power supply, peristaltic pump, electronic and associated hardware, and a connected, multi-function and handheld surgical implement, or handpiece, including a hollow slender-like needle tube as hereinabove described, in order to perform the phacoemulsification of the cataractous lens.

It should be appreciated that a surgeon utilizing the handheld implement to perform the functions hereinabove described requires easy and accessible control of these functions, as well as the ability to selectively shift or switch between at least some of the functions (for example, irrigation and irrigation plus aspiration) as may arise during phacoemulsification surgery.

In view of the difficulty with adjusting cabinet-mounted controls, while operating an associated handheld medical implement, control systems have been developed such as described in U.S. Pat. No. 4,983,901. This patent is to be incorporated entirely into the present application, including all specification and drawings for the purpose of providing a background to the complex controls required in phacoemulsification surgery and for describing apparatus which may be utilized or modified for use with the method of the present invention.

To further illustrate the complexity of the control system, reference is also made to U.S. Pat. No. 5,268,624, for "Foot Pedal Control with User Selectable Operational Ranges". This patent is to be incorporated in the present application in its entirety by this specific reference thereto, including all specifications and drawings for the purpose of further describing the state of the art in the field of this invention.

Further procedures and problems in connection with phacoemulsification, irrigation and aspiration methods and apparatus are discussed in U.S. Pat. No. 5,154,696.

It should thus be apparent, in view of the complex nature of the control system of fluids and ultrasonic power in the case of phacoemulsification procedures, that it is desirable for a surgeon to have a system which is programmable to serve both the needs of the surgical procedure and particular techniques of the surgeon, which may differ depending on the experience and ability of the surgeon.

SUMMARY OF THE INVENTION

In accordance with the present invention, a method for minimizing excess intraocular pressure during a phacoemulsification procedure in which eye tissue is fragmented and aspirated from the eye through a needle with irrigation fluid, generally includes: introducing irrigation fluid into an eye at a selected rate; aspirating the irrigation fluid while introducing the irrigation fluid at a higher rate; during phacoemulsification and aspiration of fragmented eye tissue through the needle, introducing the irrigation fluid at the higher rate; and upon occlusion or partial occlusion of the needle with fragmented eye tissue, introducing the irrigation fluid at a still higher rate.

Concomitant with minimizing excess IOP the present invention provides for controlling irrigation fluid during a surgical procedure, which includes: placing a handpiece in an operational relationship with an eye for introducing irrigation fluid thereinto; phacoemulsification of eye tissue; and aspirating fluid and fragmented eye tissue.

During aspiration the needle may become occluded or partially occluded which restricts aspiration of fluid flow through the handpiece and accordingly, in accordance with the present invention, rate of irrigation fluid flow through the handpiece is variably controlled in response to the occlusion.

BRIEF DESCRIPTION OF THE DRAWINGS

The advantages and features of the present invention will be better understood by the following description when considered in conjunction with the accompanying drawings in which.

DETAILED DESCRIPTION OF THE INVENTION

Figure 1:
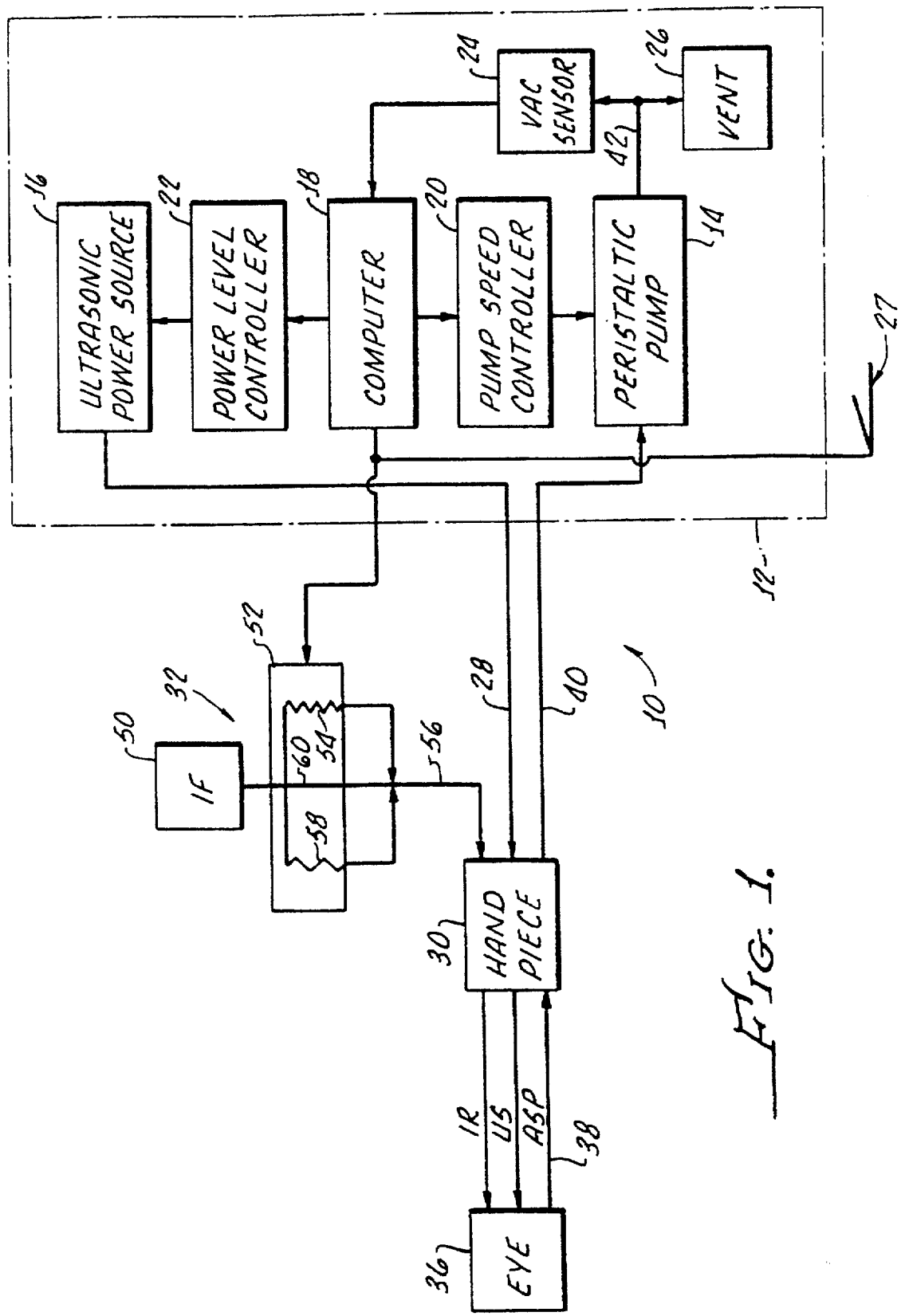
FIG. 1 is a functional block diagram of a phacoemulsification system useful for performing the method of the present invention.

Turning now to the drawings, and particularly to FIG. 1 thereof, there is shown, in functional block diagram form, a phacoemulsification system indicated generally by the reference numeral 10. The system 10 has a control unit 12, indicated by broken line in FIG. 1 which includes a variable speed peristaltic pump 14, which provides a vacuum source, a source of pulsed ultrasonic power 16, and a microprocessor computer 18 that provides control outputs to pump speed controller 20 and ultrasonic power level controller 22.

A vacuum sensor 24 provides an input to computer 18 representing the vacuum level on the output side of peristaltic pump 14. Suitable venting is provided by vent 26. A foot pedal 27 such as described in U.S. Pat. No. 5,268,624 is provide to enable a physician to control irrigation fluid flow and minimize IOP as will be hereinafter described.

The control unit 12 supplies ultrasonic power on line 28 to a phacoemulsification handpiece 30. An irrigation fluid source 32 is fluidly coupled to handpiece 30 through line 34. The irrigation fluid and ultrasonic power are applied by handpiece 30 to a patient's eye which is indicated diagrammatically by block 36. Aspiration of the eye 36 is achieved by means of the control unit peristaltic pump 14 through lines 38 and 40.

The computer 18 responds to preset vacuum levels in output line 42 from peristaltic pump 14 by means of signals from the previously mentioned vacuum sensor 24.

If the handpiece aspiration line 38 becomes occluded, the vacuum level sensed by vacuum sensor 24 will increase. The computer 18 may have operator-settable limits for aspiration rates, vacuum levels and ultrasonic power levels. When the vacuum level sensed by vacuum sensor 24 reaches a predetermined level as a result of occlusion of the handpiece aspiration line 38, computer 18 instructs pump speed controller 20 to change the speed of the peristaltic pump 14 which, in turn, changes the aspiration rate.

It should be appreciated that depending upon the characteristics of the material occluding handpiece 30, the speed of the peristaltic pump 14 can either be increased or decreased. When the occluding material is broken up, the vacuum sensor 24 registers a drop in vacuum level, causing computer 18 to change the speed of peristaltic pump 14 to an unoccluded operating speed.

The irrigation fluid source 32 may include a supply 50 interconnected to a manifold 52, or the like, for passing irrigation fluid through a flow restrictor 54 to the handpiece 30 via line 56, to provide flow at a selected rate, or through restrictor 58 or line 60 to the handpiece 30 at higher and still higher rates in accordance with the present invention, the restrictive elements being any suitable flow control well known in the art.

Figure 2:
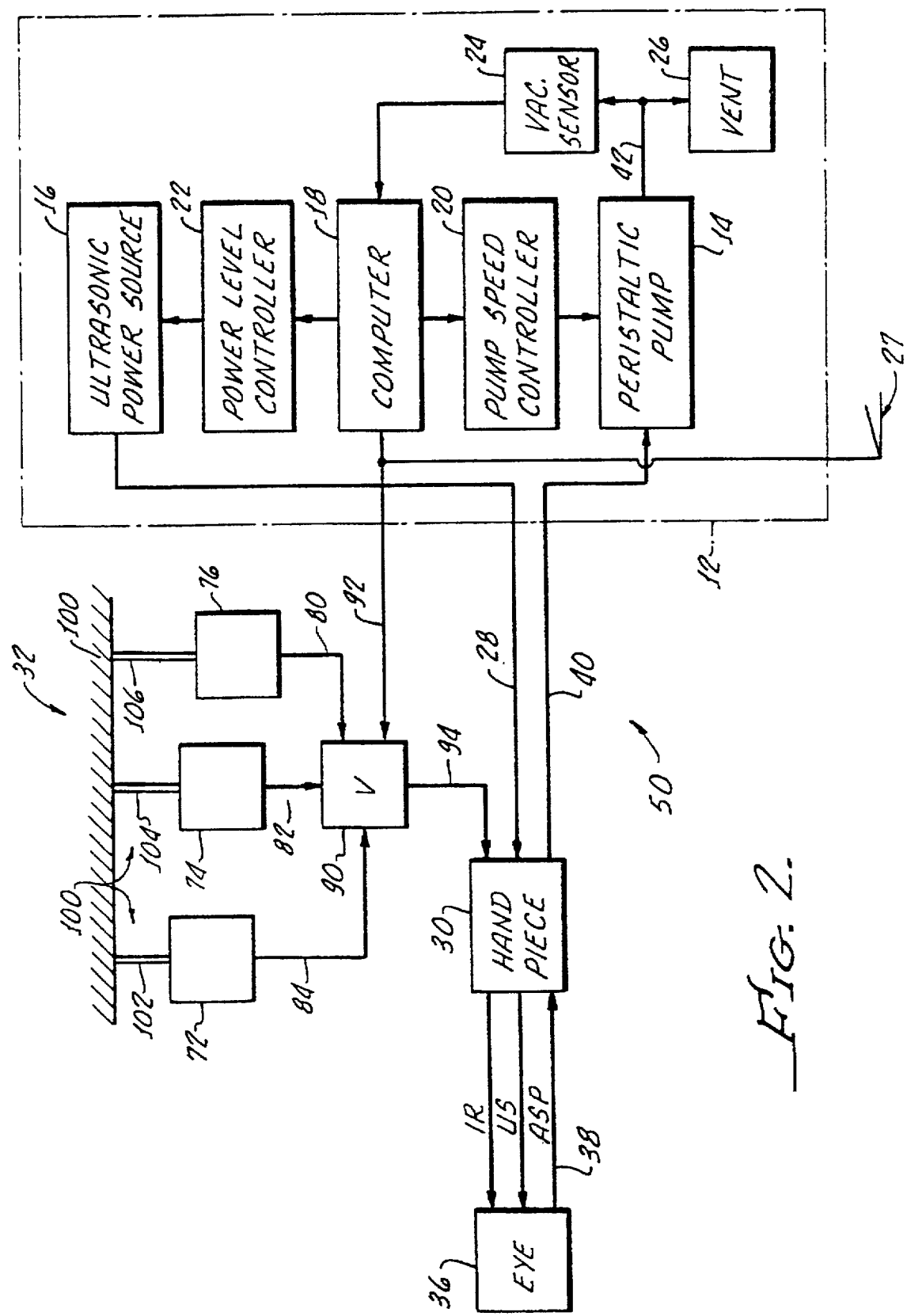
FIG. 2 is a functional block diagram of an alternative phacoemulsification system useful for performing the method of the present invention.

Turning now to FIG. 2, there is shown an alternative embodiment 70 of a phacoemulsification system, in accordance with the present invention, and which incorporates all of the elements of the system 10 shown in FIG. 1, with identical reference characters identifying components, as shown in FIG. 1. In this embodiment the irrigation fluid source 32 includes three supplies 72, 74, 76 of irrigation fluid, each disposed at a selected level above the handpiece 30 and needle thereof (not shown) for providing irrigation fluid at a selected rate, a higher rate and a still higher rate through lines 80, 82, 84 through a valve 90 controlled via the foot pedal 27 and computer 18 via line 92. The valve 90 functions to alternatively connect line 94 and supplies 72, 74, 76 with the handpiece 30 in response to a signal from the computer 18 through a the foot pedal 27.

As shown, irrigation fluid sources 72, 74, 76 are disposed at different heights above the handpiece, or needle, providing a means for introducing irrigation fluid to the handpiece at a plurality of pressures. A harness 100, including lines 102, 104, 106 of different lengths connected to a support 80, provide a means for disposing the sources, or containers, 72, 74, 76 at different heights over the handpiece 30 and needle.

Figure 3:
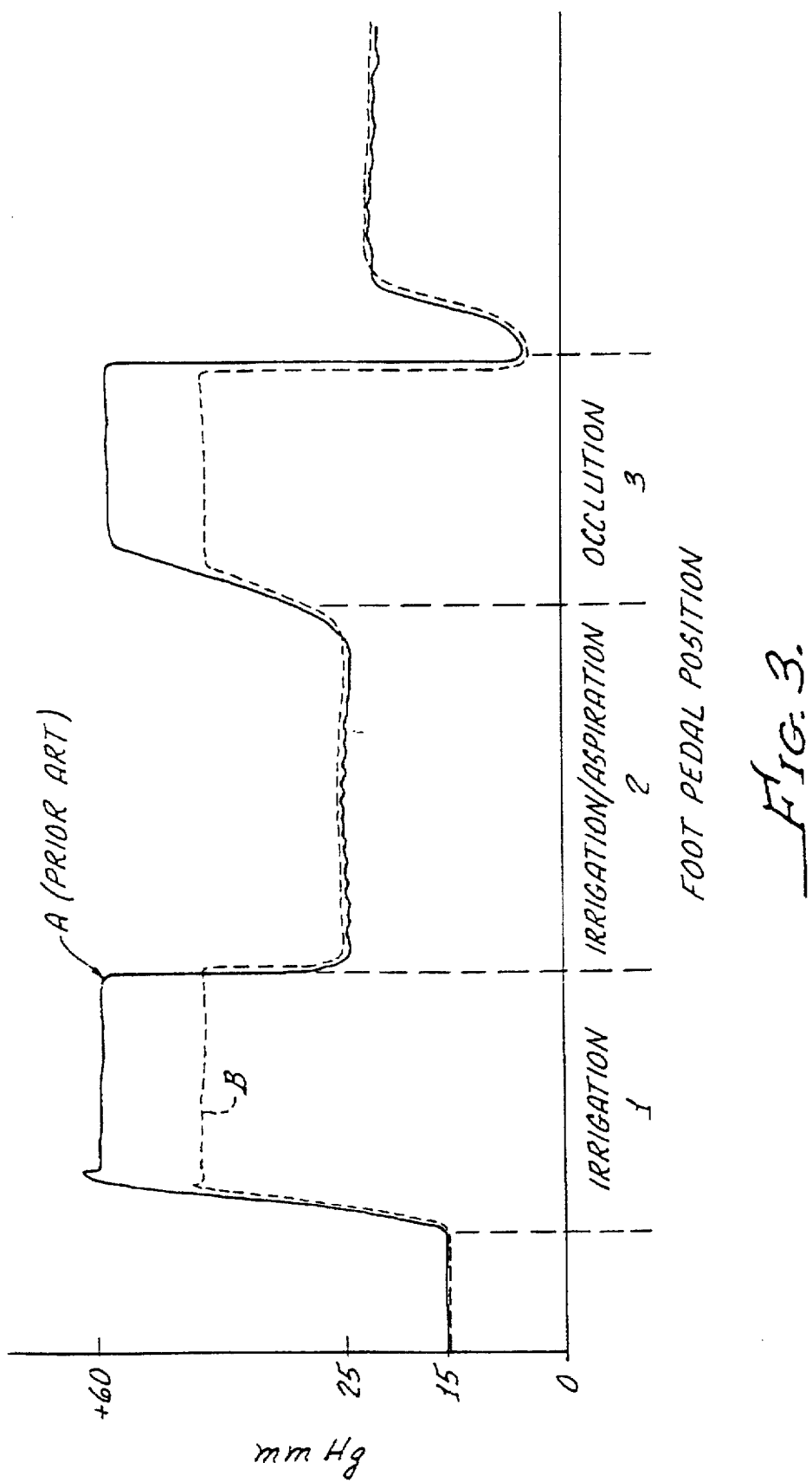
FIG. 3 is a plot of IOP as a function of procedural steps during phacoemulsification and illustrating reduced IOP provided by the method of the present invention.

Turning now to FIG. 3, there is shown Curve A, in solid line, which represents an IOP curve for heretofore methods for providing irrigation fluid during phacoemulsification procedures. In this plot, 15 mm Hg represents normal IOP in an eye. At the beginning of the procedure, irrigation fluid is provided at a rate equivalent to a pressure of 60 mm Hg.

After phacoemulsification of the eye tissue is commenced the pressure of irrigation fluid in accordance with the prior art drops slightly to about 50–60 mm Hg as shown in the figure. It should be appreciated that no separate control of irrigation fluid flow or pressure is made in prior art methods. Rather, the prevailing IOP occurs with a fixed irrigation fluid flow rate and the pressure changes therein as shown in FIG. 3 are the result of aspiration rate and the state of occlusion of the aspirating needle.

Upon partial occlusion, or total occlusion of the needle the IOP pressure increases to the irrigation fluid pressure of about 60 mm Hg as shown in FIG. 2.

Thus in accordance with prior art methods the IOP no attempt is made to control the IOP pressure through the use of variable irrigation fluid pressure or flow rate. This results in large excursions in pressure as shown in FIG. 3 which range from 60 mm Hg to 15 mm Hg based upon surges resulting from the clearing of occlusions.

This pressure pattern is in contrast to the method in accordance of the present invention in which the irrigation fluid flow rate and pressure can be controlled by a physician through a foot pedal as hereinabove described. The objective of this control is to minimize pressure changes within the eye during surgery.

The IOP pattern established in accordance with the present invention is shown in Curve B of FIG. 3. In accordance with the method of the present invention, and initial selected irrigation fluid flow rate is established by a lower pressure source 76, for example 40 mm Hg.

This flow rate is established by a foot pedal 27 position, indicated as 1 in FIG. 3. After initiation of phacoemulsification of eye tissue, ie, fragmenting thereof, aspiration of irrigation fluid and the fragmented tissue is established with a foot pedal position indicated as 2 in the plot of FIG. 3, during which a higher flow rate of irrigation fluid is established through the source 74 shown in FIG. 2. Finally, during pedal position 3 as shown in FIG. 3 a still higher irrigation fluid flow rate is established through the source 76 shown in FIG. 2 when partial or total occlusion occurs during the phacoemulsification procedures. However, it is to be appreciated that higher, lower or equivalent rates of irrigation fluid flow may be established in response to partial or total occlusion. Importantly, the present invention provides for control of irrigation fluid flow rate during phacoemulsification during surgery when partial or total occlusion occurs. That is, the irrigation fluid flow rate may be increased, decreased or held constant during partial or total occlusion.

As is evident from FIG. 3 the method of the present invention as demonstrated by Curve B results in a significant reduction in the total excess pressure (ie above 15 mm Hg.) occurring during a phacoemulsification procedure in accordance with the present invention, utilizing control of irrigation fluid flow and pressure, as opposed to prior art phacoemulsification procedures utilizing a constant irrigation fluid flow/pressure.

Although there has been hereinabove method described a method for minimizing excess intraocular pressure and a method for controlling irrigation fluid during phacoemulsification procedures in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for minimizing excess intraocular pressure during a phacoemulsification procedure in which eye tissue is fragmented and aspirated from the eye through a needle with irrigation fluid, said method comprising the steps of:

(a) introducing irrigation fluid into an eye at a selected rate;

(b) thereafter aspirating said irrigation fluid while introducing the irrigation fluid at a higher rate;

(c) during phacoemulsification and aspiration of fragmented eye tissue through the needle, introducing the irrigation fluid at the higher rate; and (d) upon partial, or total, occlusion of the needle with fragmented eye tissue, introducing the irrigation fluid at a determined rate wherein said step (a) includes providing a supply of irrigation fluid at a first selected height above the needle, said steps (b) and (c) include providing a supply of irrigation fluid at a second selected height above the needle and said step (d) includes providing a supply of irrigation fluid at a third selected height, said third selected height being greater than said second selected height, said second selected height being greater than said first selected height.

2. The method according to claim 1, wherein the determined rate is lower than the irrigation fluid rate of step (b).

3. The method according to claim 1, wherein the determined rate is equivalent to the irrigation fluid rate of step (b).

4. The method according to claim 1, wherein the determined rate is still higher than the irrigation fluid rate of step (b).

5. The method for minimizing excess intraocular pressure during a phacoemulsification procedure in which eye tissue is fragmented and aspirated from the eye through a needle with irrigation fluid, said method comprising the steps of:

(a) introducing irrigation fluid into an eye at a selected rate;

(b) thereafter aspirating said irrigation fluid while introducing the irrigation fluid at a higher rate;

(c) during phacoemulsification and aspiration of fragmented eye tissue through the needle, introducing the irrigation fluid at the higher rate; and (d) upon partial, or total, occlusion of the needle with fragmented eye tissue, introducing the irrigation fluid at a determined rate; wherein the steps (a) to (d) include providing irrigation fluid from a single supply of irrigation fluid disposed at a selected height above the needle at the selected rate, the higher rate and the still higher rate by using a manifold with output lines for the selected rate, the higher rate and the still higher rate and passing the irrigation fluid through restricted flow elements disposed in said output lines in order to establish the selected rate, the higher rate and the still higher rate of irrigation fluid in the output lines.

6. A method for controlling irrigation fluid flow into an eye during a surgical procedure, said method comprising the steps of:

(a) placing a handpiece in an operative relationship with an eye for providing irrigation fluid thereto, phacoemulsification of eye tissue and aspiration of irrigation fluid and fragmented eye tissue;

(b) introducing irrigation fluid into the eye at a selected rate before phacoemulsification of eye tissue;

(c) phacoemulsifying eye tissue while introducing irrigation fluid into the eye at a higher rate during unoccluded aspiration of the fragmented eye tissue; and (d) introducing irrigation fluid into the eye at a determined rate during partial occluded and occluded aspiration of the fragmented eye tissue wherein said step (a) includes providing a supply of irrigation fluid at a first selected height above the handpiece, said steps (b) and (c) include providing a supply of irrigation fluid at a second selected height above the handpiece and said step (d) includes providing a supply of irrigation fluid at a third selected height above the handpiece, said third selected height being greater than said second selected height, said second selected height being greater than said first selected height.

7. The method according to claim 6, wherein the determined rate is lower than the irrigation fluid rate of step (b).

8. The method according to claim 6, wherein the determined rate is equivalent to the irrigation fluid rate of step (b).

9. The method according to claim 6, wherein the determined rate is higher than the irrigation fluid rate of step (b).

10. The method for controlling irrigation fluid flow into an eye during a surgical procedure, said method comprising the steps of:

(a) placing a handpiece in an operative relationship with an eye for providing irrigation fluid thereto, phacoemulsification of eye tissue and aspiration of irrigation fluid and fragmented eye tissue; (b) introducing irrigation fluid into the eye at a selected rate before phacoemulsification of the eye tissue;

(c) phacoemulsifying eye tissue while introducing irrigation fluid into the eye at a higher rate during unoccluded aspiration of the fragmented eye tissue; and (d) introducing irrigation fluid into the eye at a determined rate during partial occluded and occluded aspiration of the fragmented eye tissue wherein the steps (a) to (d) include providing irrigation fluid from a single supply of irrigation fluid disposed at a selected height above the handpiece at the selected rate, the higher rate and the still higher rate by using a manifold with output lines for the selected rate, the higher rate and the still higher rate and passing the irrigation fluid through restricted flow elements disposed in said output lines in order to establish the selected rate, the higher rate and the still higher rate of irrigation fluid in the output lines.

* * * * *